United States Patent [19]

Stetter

[11] 4,201,634

[45] May 6, 1980

[54] METHOD FOR THE DETECTION OF HYDRAZINE

[75] Inventor: Joseph R. Stetter, Peekskill, N.Y.

[73] Assignee: Energetics Science, Inc., Elmsford, N.Y.

[21] Appl. No.: 916,296

[22] Filed: Jun. 16, 1978

[51] Int. Cl.² ............................................. G01N 27/46
[52] U.S. Cl. .................................. 204/1 T; 204/195 R
[58] Field of Search ............................ 204/1 N, 195 R

[56] References Cited

U.S. PATENT DOCUMENTS

| | | | |
|---|---|---|---|
| 2,851,654 | 9/1958 | Haddad | 204/195 R |
| 3,592,694 | 7/1971 | Urbach et al. | 204/1 N |
| 3,776,832 | 12/1973 | Oswin et al. | 204/195 R |
| 3,824,167 | 7/1974 | Oswin et al. | 204/195 R |
| 3,824,168 | 7/1974 | Oswin et al. | 204/195 R |
| 3,992,267 | 11/1976 | Oswin et al. | 204/1 N |
| 4,001,103 | 1/1977 | Blurton et al. | 204/195 R |
| 4,042,464 | 8/1977 | Blurton et al. | 204/1 N |
| 4,052,268 | 10/1977 | Blurton et al. | 204/195 R |

Primary Examiner—T. Tung
Attorney, Agent, or Firm—Larson, Taylor and Hinds

[57] ABSTRACT

Hydrazine vapors are electrochemically detected and measured by an apparatus comprising in combination intake means, an electrochemical cell, means for drawing said gas through said intake means and into said electrochemical cell, communicating means communicating said intake means with said cell, at least the internal surfaces of said intake means, said communicating means and said cell being of an inert material, the electrochemical cell comprising a sensing electrode, a counterelectrode, a reference electrode at which substantially no current flows, and an aqueous alkaline electrolyte in contact with said sensing electrode comprising a noble metal catalyst bonded to a hydrophobic material to provide a diffusion electrode, means for exposing said sensing electrode to said gas, means electrically coupled to said sensing electrode for maintaining said sensing electrode at a fixed potential of about 0.7 volt to about 1.4 volt with respect to a reversible hydrogen electrode in said electrolyte of said electrochemical cell and means for measuring current flowing from said sensing electrode to said counterelectrode which measured current is a measure of the concentration of the noxious gas being detected.

4 Claims, 3 Drawing Figures

METHOD FOR THE DETECTION OF HYDRAZINE

BACKGROUND OF THE INVENTION

1. Field of the Invention

The present invention relates to a device and method for the detection and measurement of hydrazines.

2. Discussion of the Prior Art

Hydrazines such as monomethylhydrazine and unsymmetrical dimethylhydrazine have recently found extensive use as propellants. Unfortunately, the hydrazine vapors are known or suspected of containing carcinogens exhibiting toxic effects in humans at very low, that is, ppm and ppb, levels of exposure. Consequently, it has been necessary to constantly analyze and monitor the environments in which hydrazines are used and handled to insure the safety of people living and/or working in that environment.

Such analysis of hydrazines have heretofore been accomplished by (a) colorimetric analysis, (b) stain tubes and (c) iodine titrations. Instrument techniques have also been applied to the analysis of hydrazines and include derivatization gas chromatography and chemiluminescence. The chromatographic method is non-continuous and requires a chemical vapor treatment prior to analysis while the chemiluminescence method requires prior conversion, by catalytic reaction of the hydrazine vapors, of the hydrazine to NO before detection. However, each of these methods involve a wet chemical step, are non-continuous, and do not analyze the vapors while they are in the gaseous state but require collection of the vapors in the liquid, which is normally an acid solution, or a solid support.

Another difficulty present in hydrazine gas analysis is the unusually high reactivity and/or sorption the gas exhibits with metals and like materials resulting in hydrazine sorption and decomposition reactions. Hence, attempts at analysis of the gas by instrumentation, heretofore, have failed to provide the desired accurate results.

Thus, there is a need for a cost-effective, accurate, reliable and continuous device and method for the analysis of hydrazine vapors which does not have the aforementioned drawbacks of the prior art hydrazine analytical methods.

OBJECTS AND GENERAL DESCRIPTION OF THE INVENTION

Accordingly, a primary object of the present invention is to provide a compact, cost-effective and easy-to-operate sensing apparatus for accurately and quantitatively determining the level of hydrazine pollutants in a specific environment.

Another object of this invention is to provide a compact, inexpensive, and easy-to-operate instrument exhibiting high sensitivity, selectively and reproducibility in the detection and quantitative determination of low concentrations of hydrazines in the presence of other gases.

Another object of this invention is to provide a method for electrochemically detecting low concentrations of hydrazine gases in a gaseous medium.

The aforementioned objects of the present invention are obtained by an apparatus comprising, in combination, intake means, an electrochemical cell, communicating means communicating said intake means with said cell, at least the internal surface of said communicating means being of an inert material, means for drawing said gas through said intake means and into said electrochemical cell, the electrochemical sensing electrode, a counterelectrode, a reference electrode, an aqueous alkaline electrolyte in contact with said sensing electrode, counter electrode and reference electrode, said sensing electrode comprising a noble metal catalyst supported on a hydrophobic support to provide a diffusion electrode catalyst, means for exposing said sensing electrode to the hydrazine gas to be detected, means electrically coupled to said sensing electrode for maintaining said sensing electrode at a potential of about 0.7 volt to about 1.4 volt with respect to the potential of the reversible hydrogen couple in the electrolyte of said cell and means for measuring current flowing between said sensing electrode and said counterelectrode which measured current is a measure of the concentration of the noxious hydrazine gas being detected.

An important feature of the invention is the discovery that the sensing instrument of the invention provides at an extraordinary repeatability rate, unexpectedly high sensitivity and high selectivity in the detection of very low levels of hydrazine vapor. Moreover, it has been surprisingly found that these unexpected advantages in sensitivity, selectivity and reproducibility are obtained only if there is employed the combination of (1) an aqueous alkaline electrolyte (2) a sensing diffusion electrode comprised of catalytic noble metal on a hydrophobic support (3) a three electrode system and (4) a fixed potential of about 0.7 v to 1.4 v and (5) an intake means, a means communicating the intake means with the electrochemical cell and (a) the cell whose internal surfaces are of an inert material such as plastic. Any instrument which does not possess all of these five features fails to provide the desired selectivity, sensitivity and reproducibility.

The sensing or working electrode of the invention is comprised of a noble metal catalyst capable of electrooxidation of hydrazine bonded to a suitable hydrophobic material such as unsintered polytetrafluoroethylene (PTFE) to provide a lightweight diffusion electrode. The hydrophobic material may take the form of a binder for the catalyst, a porous sheet support therefor or both. For instance, the noble metal catalytic material may be deposited as a layer directly to the surface of a hydrophobic sheet support or the catalytic particles may be admixed with a suitable hydrophobic binder and the admixture applied as a layer to suitable support such as a porous metal, porous hydrophobic sheet and the like. Suitable hydrophobic binders and/or support substrate materials include hydrophobic fluorocarbons such as polytetrafluoroethylene, polychlorotrifluoroethylene, polymeric silicones or the like, as well as hydrophobic materials including polyacrylonitrile, polyvinylchloride, polyvinylalcohol, carboxymethyl cellulose, or the like. As will be apparent to one skilled in the art, the hydrophobic material must be oriented in the cell so that the catalyst is in contact with the electrolyte and the surface of the hydrophobic substrate contacts the gas sample. Illustrative of suitable noble metals are rhodium, gold, platinum and palladium with the preferred being rhodium.

Platinum catalysts yield non-selective responses for detection of hydrazines e.g., the response for monomethylhydrazine is comparable to the response for $NO_2$. However, on gold, the reactivity is such that monomethylhydrazine can be 30 times more reactive than NO.

2. The reactivity for monomethylhydrazine on a Rhodium electrode is 70 times more reactive than $NO_2$ on the same electrode. Similar results are obtained for selectivity of the electrode CO and NO and $NH_3$. Therefore, Au and Rh electrodes can offer substantial advantages when detecting hydrazine in the presence of other gases which may be present in ambient air.

The reference electrode of the electrochemical cell must be capable of maintaining a relatively constant potential in the environment of the electrochemical cell. Preferred reference electrodes nobel metal-catalyst electrode, especially Pt-catalyzed air electrodes. The third or reference electrode can be positioned between the sensing electrode and counter electrode, or it can be positioned on the same plane or substrate as the sensing electrode or counterelectrode. Preferably, however, in order to obtain greater compactness of the cell and due to optimum ion-transfer characteristics, and the like, the counter electrode and the third or reference electrode will be part of a common substrate. It is only necessary that the electrodes of the electrochemical cell be in contact only via the electrolyte. Thus, a polymer substrate such as polytetraflorothylene can have two separate and distinct portions coated with a catalytic material such as platinum, or an admixture of platinum and PTFE particles. The entire substrate will, therefore, function as both the counter electrode and reference electrode. As will be more fully apparent hereinafter, various designs or lay-outs can be used.

Reference electrode, as the term is used herein, defines an electrode at which no, or substantially no, current flows. Accordingly, the reference electrode and sensing electrode must be connected through electronic circuitry, or the like, to preclude or minimize current flow between the reference electrode and sensing electrode, so as to define and maintain a known reference potential. Although it is virtually impossible to completely eliminate current flow, the reference potential cannot show extensive drift, i.e., more than about $\pm 24$ mV; or rapid drift, i.e., more than $\pm 4$ mV, over a period of ten seconds. If extensive or rapid drift occurs, a false reading as to the quantity of the detected gas may be obtained. As is apparent, the actual extent of current drift depends upon the accuracy of the measurement needed. If high accuracy is unnecessary, a greater current drift can be tolerated.

The specific structure of the counter electrode employed in the electrochemical cell is not critical. It is only essential that the counter electrode be comprised of a material at which electrochemical reduction occurs. In general, the counter electrode is generally a noble metal electrode such as platinum or gold electrode.

One of the problems which may be encountered in the utilization of measuring equipment such as the cell of the present invention relates to the fact that other gases such as $O_2$, $H_2O$, $CH_4$, $C_2H_6$, $C_3H_8$, $H_2$, $SO_2$, CO, $NO_2$, etc. if present in the gas sample analyzed can generate undesired current in the external circuit which current is not derived from reaction of the noxious hydrazine gas to be detected. For this reason, means are provided the electrochemical cell of the invention for maintaining the sensing electrode at a potential of about 0.7 V to 1.4 V with respect to the potential of the reversible hydrogen couple in the electrolyte of the cell. It has been found that a fixed potential within this range creates a condition whereby the hydrazine vapors being detected are oxidized without significant, if any oxidation of the other gas so that no discernible current relative to the current produced by the reaction of the hydrazine gas to be detected is produced. The means for maintaining the potential within the prescribed range can be any suitable means such as a potentiostat.

It is important that the present invention be an aqueous alkaline solution. Aqueous acid solutions fail to provide acceptable sensitivity, selectivity and reproducibility. The preferred electrolyte is aqueous KOH. The electrolyte of the invention can be free flowing or trapped in a suitable matrix and the pH of the electrolyte is generally maintained at about 8 to 14 pH units. In the event a matrix is employed, the matrix material must be sufficiently hydrophilic to permit continuous wetting of the sensing electrode and the sensing electrode and the counter electrode surfaces as well as the surface of the third or reference electrode. Materials such as asbestos, Kraft paper, polyvinylalcohol, polyvinylchloride which has been treated to render it hydrophilic or the like can be selected.

The means for measuring the current flowing from the sensing electrode to the counter electrode can be any suitable readout means such as a voltmeter or an ammeter. The reading taken at the voltmeter will be representative of the electrochemical reaction occurring at the sensing electrode an of the quantity of material reacted. The ammeter may be readily calibrated in a known manner to provide determination of the quantity of noxious gas occurring in the air sample taken.

The detecting unit of the invention includes a sample intake means and means to pass, as by pumping or drawing, the gas sample through the cell, preferably at a controlled flow rate. The control of the flow rate of the sample can be accomplished in various ways. In most instances, however, the means for drawing the gas through the intake means into the cell will effectively pass a predetermined quantity of gas per unit time to a predetermined surface area of the sensing electrode, thus assuring continuous accuracy in the quantitative measurement. Preferably, the quantity of gas fed to the sensing surface is controlled by a constant flow control means of the conventional type which feeds the gas sample to the electrochemical cell at a constant rate. Pumping or suction means are normally employed to pass the gas sample through the intake means, the electrochemical cell, and flow control means in metered amounts. Preferably, the sensing chamber will define a labyrinthine path as is described in the electrochemical cell of U.S. Pat. No. 3,766,832 hereby incorporated by reference, through which the gas sample is passed to the working electrode surface. Other designs can be employed, it only being essential that the geometric working or sensing electrode surface area remains constant, or substantially constant, and is fed with a predetermined quantity of gas over a predetermined period of time. In this regard, it is to be noted that insofar as the actual gas being detected is concerned, it is immaterial whether the flow rate is high or low.

As aforementioned, at least the internal surfaces of (1) the inlet means, (2) means communicating the inlet means with the electrochemical cell and (3) the electrochemical cell are all made of an inert material. It should be understood that the means communicating the intake means with the electrochemical cell may include pumps, filters, tubing and the like through which the sample gas may pass. The internal surfaces of these components should also be constructed of the inert material so that from the time of entry of the gas sample into the instrument until it exits from the electrochemical cell, the only apparatus surface it contacts is one of inert material.

The term "inert" as used in this specification means incapable of reacting with or sorbing hydrazine. Illustrative of inert materials that can be used are inert synthetic plastic materials, materials such as glass, alumina and metal whose surface has been treated or coated as with a base or inert plastic so as to preclude reactivity with hydrazines. Suitable synthetic plastics which can be used include, for instance, moldable synthetic thermoplastic or thermosetting polymeric materials. Polyolefins such as polyethylene, polypropylene and polystyrene and polyfluorocarbons such as polytetrafluoroethylene are preferred. Particularly preferred is "FEP Teflon" a trademarked polytetrafluoroethylene of the E. I. DuPont Company.

The external housing of the electrochemical cell can be made of any suitable material but for all practical purposes the housing will be constructed of the inert synthetic plastic as described above.

BRIEF DESCRIPTION OF THE DRAWINGS

The detecting device of the present invention will be more readily apparent from the accompanying drawing whereing like numerals are employed to designate like parts. In the drawing.

DETAILED DESCRIPTION OF PREFERRED EMBODIMENT

Figure 1:
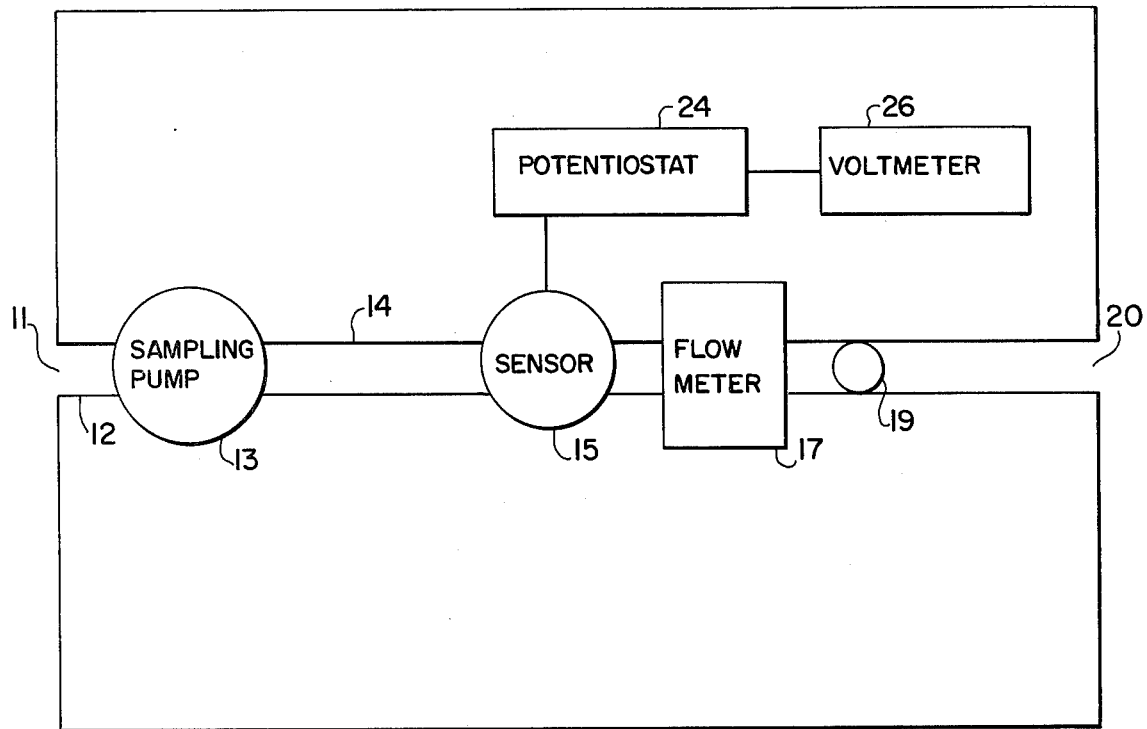
FIG. 1 is a diagrammatic view in block form of a preferred of the present invention.

More specifically, referring to FIG. 1, the detecting device for the measurement of hydrazine, such as monomethyl-hydrazine and unnsymmetrical dimethyl-hydrazine, is positioned within a housing 10. The device includes a sample intake means 11 in direct communication via line 12 with a sampling pump 13. The pump 13 communicates with the sensor (i.e. electrochemical cell) 15 via line 14 which in turn communicates with flow meter 17. Gas flowing through the sensor 15 exits device via exhaust outlet 20. A flow control means such as a valve 19 is positioned between the flow meter and exhaust 20. The sensor is provided with a potentiostat 24 for maintenance of the fixed relative potential between the anode and the reference electrode of sensor 15 and a voltmeter 26. The potentiostat is hooked up to an electronic circuit described below which includes an amplifier and voltmeter. Hydrazine intake 11, line 12, sample pump 13, line 14 and the housing sensor 15 are all constructed of FEP Teflon.

Figure 2:
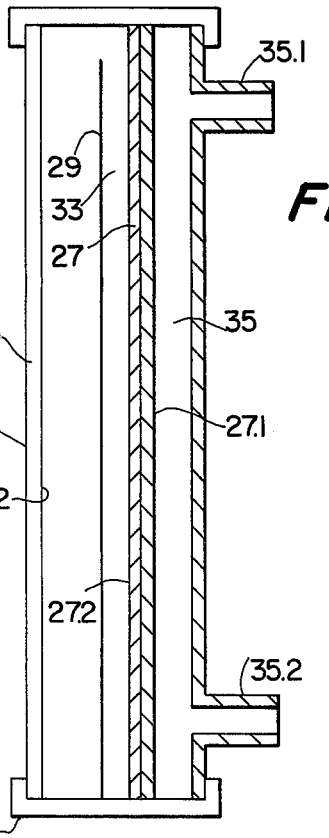
FIG. 2 is a cross-sectional view of the electrochemical cell of the detector unit.

Electrochemical sensor 15 as seen most clearly from FIG. 2, will include a cathode 25, an anode 27 (sensing electrode) and a third or reference electrode 29, all positioned within a housing 31. In the embodiment of FIG. 2, the cathode, anode, and third electrode are in contact with a free-flowing aqueous KOH electrolyte 33. Adjacent anode 27 is reactant chamber 35 having reactant gas inlet 35.1 which is in direct communication with intake 11 and outlet 35.2. In the embodiment shown, cathode 25 is in direct communication with atmospheric air. Both the anode and cathode are light-weight electrodes comprising a hydrophobic plastic substrate 27.1 and 25.1 in direct contact with reactant chamber 35 in the case of the anode, and with the ambient environment in the case of the cathode and catalytic layers 27.2 and 25.2 respectively, which catalyst layers are in contact with the electrolyte of the cell. The catalytic layer 27.2 of the sensing electrode 27 is a layer of rhodium particles and polytetrafluoro ethylene prepared by mixing the rhodium catalyst particles with an equal amount of a dispersion of the polytetrafluoroethylene particles. The resulting mixture is applied to the hydrophobic substrate 27.1 as a layer at a loading of preferably 5–50 mg/cm$^2$, more preferably 5–30 mg/cm$^2$. Catalytic layer 25.2 of the cathode 25 comprises a mixture of platinum and polytetrafluoroethylene. Reference electrode 29 is a porous, platinum catalysted PTFE diffusion electrode which is approximately 7 mils thick. A fixed potential of 1.1 volts with respect to a reversible hydrogen electrode in the same electrolyte is maintained on the anode by means of the reference electrode through the potentiostat 24. The anode, cathode and reference electrode of the cell are connected through the electrical circuit, shown in FIG. 3. The electrochemical cell of the working electrode (anode) to the counter electrode (cathode) is positive.

Figure 3:
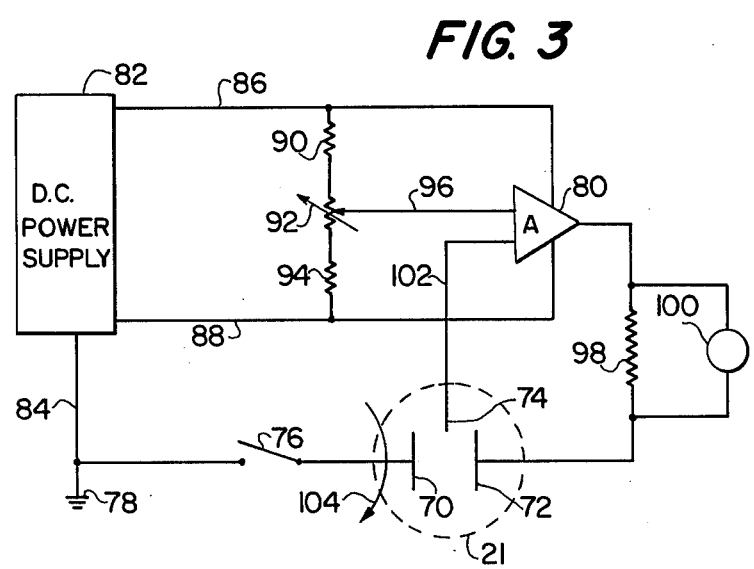
FIG. 3 is a schematic diagram of a potentiostat circuit for controlling operation of the cell and particularly as applied in maintaining a fixed potential between the working electrode and a reference electrode.

The circuitry whereby the maintenance of a fixed relative potential between the working electrode and reference electrode is shown in FIG. 3. FIG. 3 depicts a potentiostat circuit which is generally arranged in accordance with conventional principles within the knowledge of those skilled in the art and which enables the maintenance of the fixed relative potential between the working electrode and the reference electrode without development of current flow therebetween. The circuit also operates to enable appropriate current flow in the external circuit between the working electrode and the counter electrode when the gas to be detected is reacted within the electrochemical cell.

In FIG. 3, the electrochemical cell 15 is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92 and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected thereacross. The reference electrode 72 is connected to the operational amplifier 80 through a lead 102 and as the relative potential between the reference electrode 74 and the anode 70 develops a tendency to vary from the fixed level established by adjustment of the rheostat 92, the amplifier 80 operates through a negative feedback to maintain constant the relative potential between the anode 70 and the reference electrode 74. The factor creating the tendency to alter the anode reference electrode fixed relative potential is developed as a result of reaction at the anode 70 of the impurity to be detected, i.e. oxidation of MMH contained within the gas sample flowing across the face of the anode 70 as indicated by the arrow 104. The output current of the operational amplifier 80 will pass through the resistor 98 and will be a result of and related to the level of oxidation occurring at the anode 70. Therefore, the reading taken at the voltmeter 100 will be representative of the oxidation reaction occurring at the anode 70 and the quantity of material oxidized.

In operation, therefore, assuming the desirability of measuring the concentration of hydrazine(monomethylhydrazine or unsymmetrical-dimethylhydrazine) in the atmosphere, the atmospheric air containing the noxious gas is introduced into inlet 11 and pumped by pump 13 through line 14 at a metered rate into the sensor. In sensor 15 the air sample passes over the anode therein setting off electrooxidation of the hydrazine impurity contained therein. This electrochemical reaction produces a current in the external circuit of the cell thereby enabling detection and measurement of the impurity concentration as by use of a voltmeter.

It is claimed:

1. A method for electrochemically detecting a hydrazine gas which comprises the steps of (1) feeding a gaseous sample containing said gas from an intake means to a sensing electrochemical cell through means communicating said intake means with said cell, at least the internal surfaces of said intake means, said communicating means and said cell being of a material inert to hydrazine, said electrochemical cell comprising a sensing electrode, a counter electrode, and a reference electrode at which substantially no current flows, an aqueous alkaline electrolyte in contact with said sensing electrode, counter electrode and reference electrode, said sensing electrode comprising a noble metal catalyst bonded to a hydrophobic material to provide a diffusion electrode; (2) maintaining said sensing electrode at a fixed potential of about 0.70 volt to 1.4 volts with respect to the potential of the reversible hydrogen couple in the electrolyte of said cell; and (3) measuring the current flowing between said sensing electrode and counter electrode of said cell to quantitatively determine the amount of said hydrazine gas in said gaseous sample.

2. The method of claim 1 wherein the catalyst comprises rhodium.

3. The method of claim 1 wherein the catalyst comprises gold.

4. The method of claim 1 wherein the hydrophobic material is polytetrafluoroethylene.

* * * * *